United States Patent
Subramanian et al.

(10) Patent No.: US 6,896,850 B2
(45) Date of Patent: May 24, 2005

(54) SILICON NITRIDE WINDOW FOR MICROSAMPLING DEVICE AND METHOD OF CONSTRUCTION

(75) Inventors: Kumar Subramanian, Pleasanton, CA (US); Wilson Smart, Palo Alto, CA (US); Asikeh Kanu, Oakland, CA (US)

(73) Assignee: Kumetrix, Inc., Union City, CA (US)

( * ) Notice: Subject to any disclaimer, the term of this patent is extended or adjusted under 35 U.S.C. 154(b) by 288 days.

(21) Appl. No.: 09/816,497

(22) Filed: Mar. 26, 2001

(65) Prior Publication Data

US 2002/0136667 A1 Sep. 26, 2002

(51) Int. Cl.$^7$ ................................................. B01L 3/00
(52) U.S. Cl. .................. 422/102; 422/55; 422/68.1; 422/99; 422/100; 436/165; 436/174; 436/179
(58) Field of Search ................... 422/55, 58, 61, 422/60.1, 99, 100, 102; 436/164, 165, 174, 179; 435/283.1, 287.1, 288.1, 288.7; 156/625.1, 626.1, 662.1

(56) References Cited

U.S. PATENT DOCUMENTS

| | | | | |
|---|---|---|---|---|
| 3,597,046 A | * | 8/1971 | Smithgall | 350/164 |
| 4,468,282 A | | 8/1984 | Neukermans | |
| 4,784,721 A | * | 11/1988 | Holmen et al. | 156/647 |
| 5,005,058 A | * | 4/1991 | Tanaka | 357/17 |
| 5,074,629 A | * | 12/1991 | Zdeblick | 385/14 |
| 5,285,131 A | * | 2/1994 | Muller et al. | 313/578 |
| 5,358,746 A | * | 10/1994 | Bruck et al. | 427/376.2 |
| 5,493,177 A | * | 2/1996 | Muller et al. | 313/578 |
| 5,578,517 A | * | 11/1996 | Yoo et al. | 437/60 |
| 5,668,376 A | * | 9/1997 | Weckstrom et al. | 250/495.1 |
| 5,728,089 A | | 3/1998 | Lal et al. | |
| 5,801,057 A | * | 9/1998 | Smart et al. | 436/68 |
| 5,870,482 A | * | 2/1999 | Loeppert et al. | 381/174 |
| 5,925,479 A | * | 7/1999 | Wei et al. | 429/91 |
| 6,002,202 A | | 12/1999 | Meyer et al. | |
| 2002/0160520 A1 | * | 10/2002 | Orloff et al. | 436/72 |

OTHER PUBLICATIONS

Ciarlo, Dino R.; "Silicon Nitride Thin Windows for Biomedical Microdevices"; *Biomedical Microdevices* 4:1, pp. 63–68, 2002.

Goncz, K. K. et al.; "An environmental sample chamber for X-ray microscopy"; *Journal of Microscopy*, vol. 168, Pt 1, Oct. 1992, pp. 101–110.

* cited by examiner

*Primary Examiner*—Jill Warden
*Assistant Examiner*—Dwayne K Handy

(57) ABSTRACT

A silicon nitride cuvette window for a microsampling device and method of construction are provided. The sample to be analyzed is drawn into the cuvette of the microsampling device. The silicon nitride window permits optical measurements to be made on analytes contained within the cuvette.

11 Claims, 3 Drawing Sheets

SILICON NITRIDE WINDOW FOR MICROSAMPLING DEVICE AND METHOD OF CONSTRUCTION

TECHNICAL FIELD

This invention relates generally to a window constructed of silicon nitride, and more particularly to a cuvette window of a microsampling device and a method of construction.

BACKGROUND

Diabetes mellitus is an insidious disease which affects more than 15 million Americans. About 1.5 million of these are Type I diabetics (insulin-dependent) and 12 to 14 million are Type II diabetics (noninsulin-dependent). The characteristics of diabetes include chronic and persistently high levels of glucose in blood and in urine. Although urine glucose has been used to monitor glucose levels, the measurement of blood glucose is more reliable and logistically feasible. Blood glucose has therefore become the most commonly followed clinical marker for monitoring the progress of diabetes (and other diseases) to determine treatment and control protocols. Glucose levels are routinely measured in doctors' offices, clinical laboratories, and hospitals. However, the most convenient and important measuring is in-home self-monitoring of blood glucose levels by the patients themselves to permit adjustment of the quantities of insulin and hypoglycemics administered.

There are many products for diabetes related testing of glucose for diagnostic and monitoring purposes. Most of the currently available technologies, especially for self-monitored blood glucose measurements, are not satisfactory because they require some kind of deep lancing or finger stick with associated pain and sometimes excessive bleeding.

The smallest lancet or needle currently marketed for blood sampling has a diameter between 300 micrometers and 500 micrometers, and is constructed of stainless steel with beveled edges. Due to the large cross-section of these lancets, fingertip lancing is painful and frequent lancing causes calluses, impairment of the use of hands, psychological trauma and other unpleasant consequences. Further, blood samples recovered from the patient must be transferred to a test strip or cartridge for assaying analyte concentrations. Obtaining blood samples by lancing and performing the analysis can be messy as well as painful for the patient.

U.S. Pat. No. 5,801,057, "Microsampling Device and Method of Construction," issued Sep. 1, 1998, to Wilson H. Smart and Kumar Subramanian, describes a self-contained microsampling device and method for the measurement of glucose and other analytes in blood. Blood is drawn through a microneedle sufficiently small that the sampling is virtually painless into an integrated microcuvette where the analyte concentration is measured. The microsampling device of Smart et al has two windows, namely, a glass film for one window and a glass wafer for the other window. While these windows provide excellent transparency and functionality, the application of semiconductor processing to glass is less well established than is the case for silicon nitride. A silicon nitride cuvette window can be directly integrated with the other components of the microsampling device using standard semiconductor processing.

Unsupported silicon nitride films are used as membranes in products such as condenser microphones and pressure sensors. Supported films are used in electronics applications. In Yoo et al, U.S. Pat. Nos. 5,578,517 and 5,729,041, a silicon nitride film is used to form a transparent window covering a fusible link. The window is fully supported on the fusible link or other substrate materials, however. Further, the window is not used to permit optical measurements but rather to permit laser irradiation of the fusible link.

SUMMARY

There still exists a need for simplification in the manufacturing process of a microsampling device which provides reliable and accurate measurements of glucose and other analytes. Furthermore, there still exists a need for a chamber (cuvette) window for such microsampling device which can be fabricated by standard semiconductor processing methods, which is able to withstand normal handling, and which is transparent to light in the desired visible regions, permitting accurate optical measurements. A microsampling device with microneedle and sampling chamber or cuvette fabricated wholly out of silicon with silicon nitride windows can be manufactured by standard semiconductor processing methods with precision and accuracy and at low unit cost.

It is an object of this invention, therefore, to provide a cuvette window of a microsampling device which is economical to fabricate, transparent at visible wavelengths, and able to withstand normal handling, and a process for its construction.

It is a further object of this invention is to provide a cuvette window of a microsampling device, formed by a silicon nitride film deposited on the microsampler chamber of the microsampling device with the film being exposed on both surfaces.

Supported silicon nitride films are widely used in semiconductor processing, primarily for masking. In order to use an unsupported film as an optical window, its deposition must be carefully controlled to produce a low stress film. This is a standard procedure in the optics industry, where the deposition of optical coatings is closely monitored to control variations in optical properties. Stress in silicon nitride films is decreased in two ways. First, the stoichiometric ratio of the silicon nitride composition is chosen to provide as close a match as possible to the coefficient of expansion of the silicon substrate. Second, plasma enhanced deposition is used. Optionally, application of an antireflective coating such as magnesium fluoride on the silicon nitride film will further improve the optics of these windows, permitting their use for optically read assays without contributing any significant error to the assay result.

It is a further object of this invention to provide a method of constructing a cuvette window for a microsampling device. The method utilizes standard semiconductor processes, permitting the window to be readily integrated into the fabrication of other microsampler components.

It is a further object of this invention is to provide a window of a silicon sampling chamber or cuvette, formed by a silicon nitride film deposited on the chamber of the cuvette with the film being exposed on both surfaces.

The silicon cuvette with silicon nitride window can be used for measurement of analytes other than blood or fluids accessed through the microneedle of the microsampling device. These analytes can be introduced thorough a vent or directly into the cuvette. Further, silicon nitride film windows as large as approximately 1 square centimeter can be fabricated with satisfactory handling and optical characteristics, thus permitting semiconductor technology to be used to fabricate cuvettes with integrated silicon nitride windows which can be larger than the chamber of the microsampling device.

It is a further object of this invention to provide a method of constructing a window for a sampling chamber or cuvette fabricated of silicon. The method utilizes standard semiconductor processes, permitting the window construction to be readily integrated into the processes used to fabricate the cuvette.

Briefly, these and other objects of the present invention are accomplished by providing a cuvette window for a microsampling device and method for its construction. The cuvette window comprises a silicon nitride film deposited in a microsampler chamber etched into the surface of the silicon wafer, with a portion of the film being exposed on both sides. The silicon nitride window so formed can be fabricated by standard semiconductor processing methods, is able to withstand normal handling, and transmits light in the visible region.

DETAILED DESCRIPTION OF THE PREFERRED EMBODIMENTS

Figure 1A:
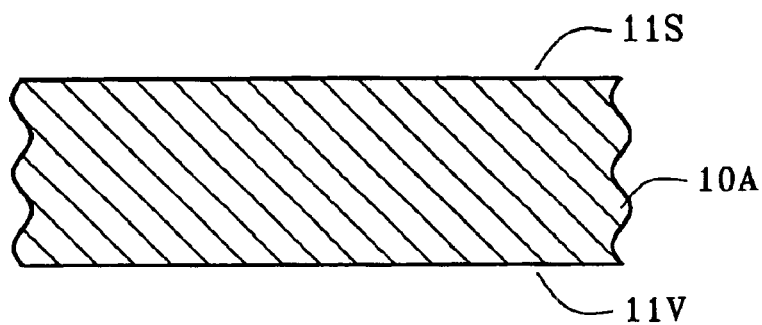
FIG. 1A is a section view of a silicon wafer prior to initial patterning and etching.

The present invention comprises a process of constructing a cuvette window for a microsampling device for the measurement of biological materials from biological fluids. the microsampling device is preferably fabricated from a silicon wafer and is generally described in U.S. Pat. No. 5,801,057, by Smart et al., the subject matter of which is hereby incorporated by reference in its entirety into this disclosure. FIGS. 2A, 2B, and 2C, herein, depict the microsampling device of the '057 patent and are reproduced from FIGS. 1, 2A and 2B of the '057 patent. The same element numbers have been used FIGS. 2A, 2B and 2C increased by 200 over the element numbers used in the corresponding figures of the '057 patent.

As shown in FIG. 2A, the microsampling device or microsampler of the present invention 210 has a very fine, short needle 211 through which blood or other body fluids can be drawn into a small sampling chamber (microcuvette) 212 which preferably has a volume of less than one microliter. Sampling chamber 212 has at least one optical window 213 and a vent 214 to allow air to escape as the camber fills when blood or other fluids are drawn in through needle 211. Needle 212 preferably has an outer diameter of 100 to 200 microns, compared to at least 425 microns for the smallest lancet currently available.

An exemplary design of microsampler 215 is shown in FIGS. 2B and C. Needle 216 is formed as an etched channel (bore) 217 in silicon and sealed with glass cover 221 hermitically bonded to the silicon. The silicon body 218 contains a sampling chamber 219 from which needle bore 217 and vent 220 extend as an integral part thereof. The top of microsampler 215 is covered by cover glass 221 which forms an optical window for chamber 219 and also covers needle bore 217. Glass 222 deposited at the bottom of microsampler 215 forms a second optical window opposite optical window from camber 219. Glass 222 is deposited at the bottom of a depression 223 formed in silicon body 218.

Although the needle 216 may have an outer diameter in the range of 30 to 300 microns and a bore diameter in the range of 25 to 250 microns, in the exemplary embodiment, needle 216 has an outer diameter of 100 microns, a bore diameter of 50 microns, and a length of about 3 mm. Silicon bode 218 is about 5 mm×5 mm square, and chamber 219 is about 2 mm×2 mm square. Silicon body 218 has a thickness of about 500 microns to 1 mm. Chamber 219 has a depth of about 50 microns and cover glass 221 has a thickness of about 150 microns.

The present invention has a transparent window on the silicon wafer to facilitate optical readouts of the specimen within the cuvette. Optical quality silicon nitride film is deposited on the silicon wafer and silicon removed such that a portion of the film is exposed on both sides.

The microsampling device or microsampler has a very fine, short needle though which blood or other body fluids can be drawn into a small sampling chamber or microcuvette. Preferably, the microcuvette has a volume of less than one microliter. The microcuvette has at least one optical window and a vent to allow air to escape as the microcuvette fills when blood or other fluids are drawn in through the needle. The needle preferably has an outer diameter of 100 to 200 micrometers.

The microsampler is constructed using well-established silicon microfabrication technology which has been in wide use for decades for the manufacture of electronic integrated circuits and more recently has been extended to micromechanical devices. The microsampler is made by a series of very precise photolithographic, etching and very precise microdeposition steps performed on a silicon wafer. A large number of the present microsampling device can be made at the same time on a single wafer, followed by dicing to separate the individual devices, each of which is commonly referred to as a die or chip in the microelectronics industry.

The cuvette window comprises a silicon nitride film formed on the microsampler chamber of the microsampler device with the window being exposed on two surfaces. The method of construction comprises providing a silicon wafer having a top surface 11S (sampling side) and a bottom surface 11v (viewing side), etching a patterned depression in the top surface of the silicon wafer thereby defining the microsampler chamber, depositing a silicon nitride film on the top surface of the silicon wafer, and etching a patterned depression in the bottom surface of the silicon wafer such that at least a portion of the silicon nitride film deposited in the microsampler chamber becomes exposed on both surfaces.

The stages or steps of the cuvette window fabrication process are illustrated in FIGS. 1A–1D, and are described in further detail below. The microsampling device may have one or two cuvette windows, depending on the detection method used. A two window device suitable for analyte detection using transmittance photometry can be fabricated from two wafers where the cuvettes and windows are bonded together in registration. Alternately, the second window can be provided separately in the device holder. A microsampling device with only one cuvette window is used where the methods of choice for the detection of the analyte may be fluorescence, luminescence, or reflectance photometry. In this case, a blank silicon wafer is bonded to the wafer containing the cuvettes and windows, and the individual devices then separated.

Figure 2A:
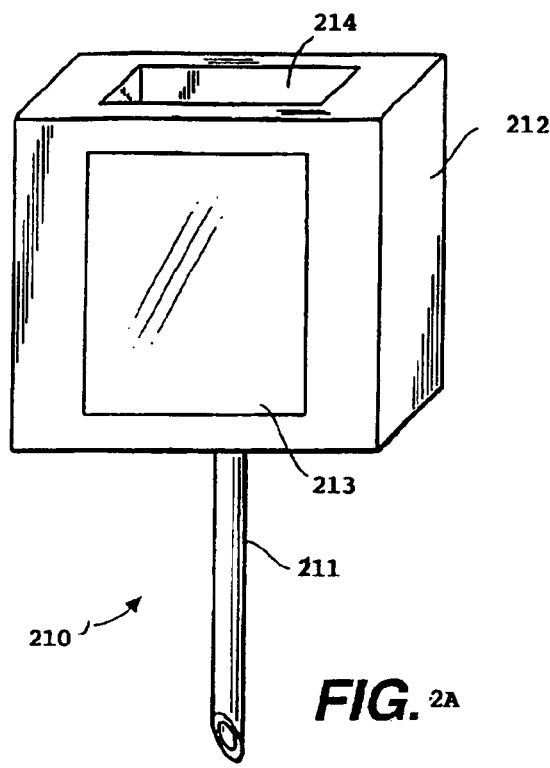
FIG. 2A is a perspective view of a microsampling device.
Figure 2B:
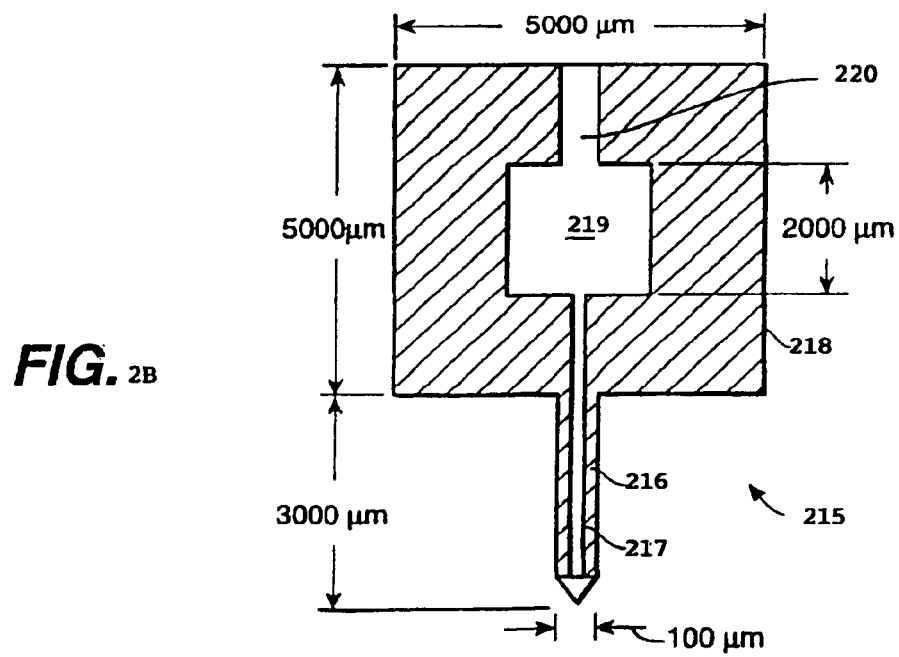
FIG. 2B is a top view of the microsampling device of FIG. 2A.
Figure 2C:
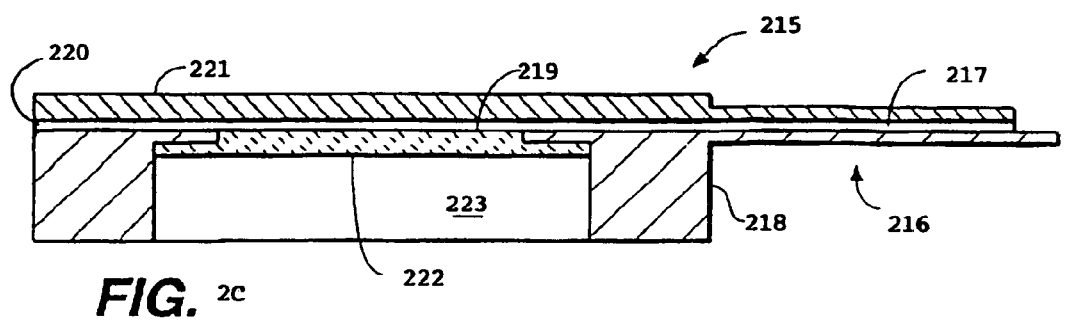
FIG. 2C is a side view of the microsampling device of FIG. 2A.

In the present example, a silicon wafer about 500 micrometers thick having one surface polished forms silicon substrate 10a of the microsampling device as illustrated in FIG. 1A. Silicon wafers of this type are commercially available and are commonly used in the integrated circuit industry in thickness of 500 to 1000 micrometers.

Figure 1B:
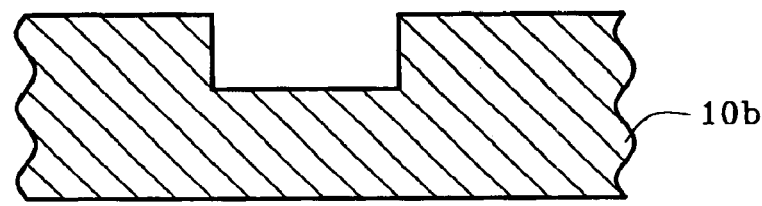
FIG. 1B is a section view of the silicon wafer of FIG. 1A subsequent to etching of the top surface to define the sampling chamber.
Figure 1C:
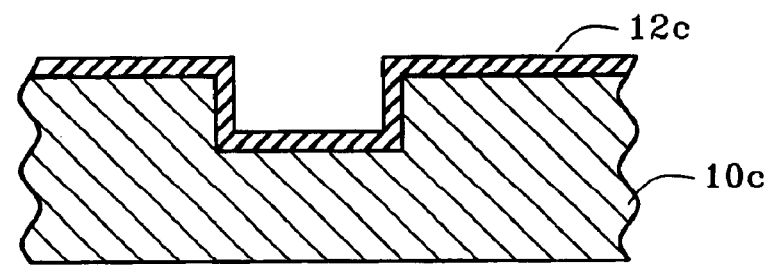
FIG. 1C is a section view of the silicon wafer of FIG. 1B showing a silicon nitride film layer deposited on the top of the etched wafer.

Silicon substrate 10a is first patterned and plasma etched on the top polished surface to form the vent, cuvette, and needle bore pattern required for operation of the microsampling device. FIG. 1B illustrates the microsampler chamber or cuvette in silicon substrate 10b subsequent to the plasma etching. As illustrated in FIG. 1C, low stress silicon nitride film 12c is then deposited onto the top surface of silicon substrate 10c. The silicon nitride film has a thickness of approximately 0.01 to 5 micrometers.

Figure 1D:
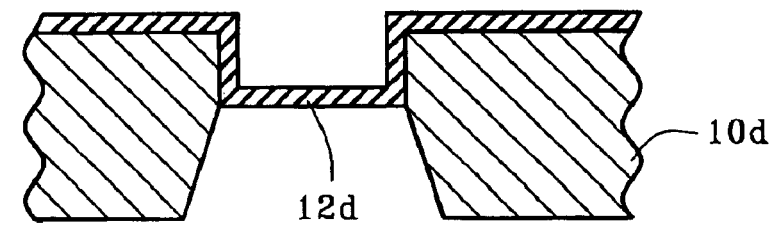
FIG. 1D is a section view of the silicon wafer of FIG. 1C with deposited silicon nitride film subsequent to etching the bottom of the wafer to remove the silicon in the window region and expose the bottom of the silicon nitride film.

As illustrated in FIG. 1d, the bottom of silicon wafer 10d is then etched with a potassium hydroxide wet etchant to remove silicon and expose the bottom of silicon nitride window 12d.

INDUSTRIAL APPLICABILITY

It will be apparent to those skilled in the art that the objects of this invention have been achieved as described hereinbefore by providing a silicon nitride cuvette window for a microsampling device. The silicon nitride window provides at least three advantages. First, the cuvette window can be fabricated by standard semiconductor processing methods. Second, the cuvette window is substantially transparent in the desired wavelengths. Finally, the cuvette window withstands normal handling in course of using the microsampling device.

CONCLUSION

The foregoing description of the preferred embodiments of the subject invention have been presented for purposes of illustration and description and for a better understanding of the invention. It is not intended to be exhaustive nor to limit the invention to the precise form disclosed. Modifications and variations are possible without departing from the concept of the invention. For example, additional coatings, such as antireflection coatings, can be added on top of the silicon nitride window to improve optical properties. Therefore, the scope of the invention is to be determined by the terminology of the following claims and the legal equivalents thereof.

What is claimed is:

1. Method of constructing a window in a silicon cuvette, comprising the steps of:
   providing a silicon substrate having a top surface and a bottom surface;
   etching a depression in the top surface of the silicon substrate defining a microsample chamber;
   depositing a silicon nitride film on the top surface of the silicon substrate and in the chamber; and
   etching a depression in the bottom surface of the silicon substrate in registration with the chamber in the top surface for exposing the silicon nitride film within the chamber to form the window.

2. The method of claim 1 wherein the silicon substrate is a silicon wafer.

3. The method of claim 1 wherein the silicon nitride film has a thickness of from about 0.01 of a micrometer to 5 about micrometers.

4. Method of constructing a chamber window in a microsample chamber, comprising the steps of:
   providing a silicon substrate having a sampling side and a viewing side;
   etching a depression in the sampling side of the silicon substrate defining a microsample chamber, a needle bore, and a vent;
   depositing a silicon nitride film in at least the microsample chamber; and
   etching a depression in the viewing side of the silicon substrate in registration with the microsample chamber in the sampling side for exposing the silicon nitride film within the microsample chamber to form the chamber window.

5. The method of claim 4 wherein the silicon substrate has a thickness of about 500 micrometers.

6. The method of claim 4 wherein the silicon nitride film has a thickness of from about 0.01 of a micrometer to about 5 micrometers.

7. The method of claim 4 further comprising the step of applying an antireflective coating to the exposed silicon nitride film.

8. The method of claim 7 wherein the applied antireflective coating is magnesium fluoride.

9. The method of claim 1 further comprising the step of applying an antireflective coating to the exposed silicon nitride film.

10. The method of claim 9 wherein the applied antireflective coating is magnesium fluoride.

11. Method of constructing a window in a silicon cuvette, comprising the steps of:
    providing a silicon substrate having a top surface and a bottom surface;
    etching a depression in the top surface of the silicon substrate defining a microsample chamber;
    depositing a silicon nitride film in at least the chamber; and
    etching a depression in the bottom surface of the silicon substrate in registration with the chamber in the top surface for exposing the silicon nitride film within the chamber to form the chamber window.

* * * * *